(12) United States Patent
Bessler et al.

(10) Patent No.: US 7,211,114 B2
(45) Date of Patent: May 1, 2007

(54) ENDOSCOPIC GASTRIC BYPASS

(75) Inventors: Marc Bessler, Teaneck, NJ (US); John D. Allendorf, Sleepy Hollow, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/229,400

(22) Filed: Aug. 26, 2002

(65) Prior Publication Data

US 2004/0039452 A1    Feb. 26, 2004

(51) Int. Cl.
*A61F 2/04* (2006.01)

(52) U.S. Cl. .................................... 623/23.65
(58) Field of Classification Search ............. 623/1.15, 623/23.68; 604/43
See application file for complete search history.

(56) References Cited

U.S. PATENT DOCUMENTS

| | | | |
|---|---|---|---|
| 4,134,405 A | 1/1979 | Smit | |
| 4,501,264 A | 2/1985 | Rockey | |
| 4,846,836 A | 7/1989 | Reich | |
| 5,180,364 A | 1/1993 | Ginsburg | |
| 5,306,300 A * | 4/1994 | Berry | 623/23.64 |
| RE35,849 E | 7/1998 | Soehendra | |
| 5,820,584 A | 10/1998 | Crabb | |
| 5,824,071 A * | 10/1998 | Nelson et al. | 606/194 |
| 6,254,642 B1 | 7/2001 | Taylor | |
| 6,261,305 B1 | 7/2001 | Marotta et al. | |
| 6,264,700 B1 | 7/2001 | Kilcoyne et al. | |
| 6,302,917 B1 * | 10/2001 | Dua et al. | 623/23.68 |
| 6,675,809 B2 * | 1/2004 | Stack et al. | 128/898 |
| 6,845,776 B2 | 1/2005 | Stack et al. | |
| 2002/0062146 A1 * | 5/2002 | Makower et al. | 623/1.13 |
| 2003/0199991 A1 | 10/2003 | Stack et al. | |
| 2004/0117031 A1 | 6/2004 | Stack et al. | |
| 2004/0138761 A1 | 7/2004 | Stack et al. | |

* cited by examiner

*Primary Examiner*—Corrine McDermott
*Assistant Examiner*—Christopher D Prone
(74) *Attorney, Agent, or Firm*—Wolf, Block, Schorr & Solis-Cohen LLP; William H. Dippert

(57) ABSTRACT

An endoscopic device separates ingested food from gastric fluids or gastric fluids and digestive enzymes, to treat obesity. In a particular embodiment a gastric bypass stent comprises a tubular member and two or more stent members defining a lumen. The tubular member has a substantially liquid impervious coating or covering and one or more lateral openings to permit one-way liquid flow.

31 Claims, 2 Drawing Sheets

ENDOSCOPIC GASTRIC BYPASS

FIELD OF THE INVENTION

The invention disclosed herein relates to a method and device for treating obesity. More particularly, the invention relates to a method and device wherein a covered stent having at least one one-way valve is positioned to extend from a patient's gastro-esophageal junction to the patient's duodenum.

BACKGROUND OF THE INVENTION

Surgical treatment of morbid obesity dates back to 1954 when the first jejunoileal bypass (intestinal) was done specifically for weight loss. The premise of this bypass was that patients could eat large amounts of food and the excess would either be poorly digested or passed along too rapidly for the body to absorb excess calories. In addition, intestinal bypass caused a temporary decrease in appetite which also resulted in weight loss. Unfortunately, essential nutrients were also lost in the stool. Because the effects of intestinal bypass were too difficult to predict and manage, the original form of the operation is no longer performed.

In 1969 it was noted that near-total removal of the stomach for cancer or ulcers caused patients to remain at below normal weight. This suggested that a gastric bypass could be used for severe obesity. This approach involved stapling off most of the stomach, bypassing the duodenum, and allowing the undigested food to pass along directly into the intestine. Most of the early operations eventually failed because the pouch became enlarged.

Today there are two primary surgical procedures used for achieving weight loss. One is the vertical banded gastroplasty, commonly referred to as VBG, and the other is the Roux-en-Y gastric bypass, or simply, the gastric bypass.

Gastric bypass involves significant enough risk to a patient that it is considered only as a lifesaving undertaking for morbidly obese individuals. Reported complications following the gastric bypass include postoperative complications and side effects such as marginal ulcers, wound infections, pulmonary emboli, gastrointestinal hemorrhage, renal failure, and numerous other disorders. The nature, severity, and frequency of these problems have in fact led some to doubt the advisability of the known surgical techniques for treatment of obesity. There has been, and continues to be, a need for less traumatic surgical or non-surgical techniques to treat obesity.

OBJECTS OF THE INVENTION

It is an object of the invention to provide a method and device for treating obesity.

It is also an object of the invention to provide an endoscopic device to separate ingested food and gastric fluids.

It is a further object of the invention to provide an endoscopic device to separate ingested food in the small bowel from digestive enzymes.

It is additionally an object of the invention to provide a covered stent having one-way valves.

It is a yet further object of the invention to provide a method for treating obesity wherein a covered stent having one-way valves is inserted into a patient's gastrointestinal tract.

These and other objects of the invention will become more apparent from the discussion below.

SUMMARY OF THE INVENTION

According to the invention, a device is inserted into a patient's stomach endoscopically to separate ingested food from gastric fluids and, optionally, to separate ingested food in the duodenum from digestive enzymes. In one embodiment of the invention, a stent is inserted into a patient's gastrointestinal tract to bypass the stomach. The stent comprises a covered stent having one-way openings and/or valves on its annular surface and preferably at least one one-way valve at one end to permit entry of food and/or liquids. Optionally the one-way valve at the end of the stent can comprise a sleeve that extends through the stent, preferably into the duodenum or beyond. One end of the stent is intended to be positioned at or above the gastro-esophageal junction, and the other end is intended to be positioned in the duodenum or beyond. The net effect of endoscopic gastric bypass is to replicate some or all of the effects of a surgical gastric bypass.

The stent is advantageously delivered on a balloon dilatation catheter having one or more dilatable balloons. Preferably the distal and proximal portions of the stent are attached or crimped to corresponding portions of the catheter, and then, when the stent is properly positioned, balloons are dilated to expand the stent portions. Self-expanding stents, with appropriate catheter-based delivery systems, could be used as well. The stent can be removed by use of one or more of known methods or devices.

DETAILED DESCRIPTION OF THE INVENTION

Figure 1:
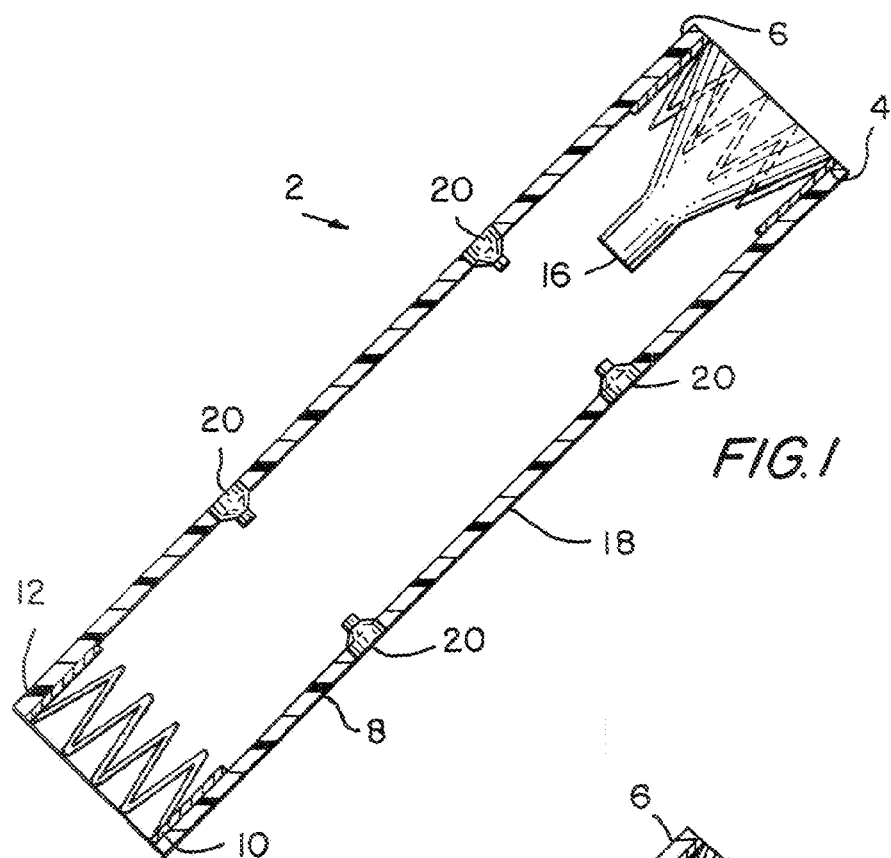
FIG. 1 is a partly cross-sectional view of an embodiment of the invention.

The invention can perhaps be better appreciated by making reference to the drawings. In FIG. 1, a gastric bypass stent 2 comprises a stent member 4 at the proximal end 6 of a tubular member 8 and, optionally, a stent member 10 at the distal end 12 of tubular member 8. Proximal tubular end 6 comprises a one-way valve member 16 to permit passage of food and liquid, and the wall 18 of tubular member 8 comprises oneway openings or valves 20 to permit gastric acid or fluid to flow into stent 2.

Optionally stent 2 could comprise one or more stent members 4, 10 that would together define a lumen and would have a coating or surface that would be the functional equivalent of tubular member 8.

Figure 2:
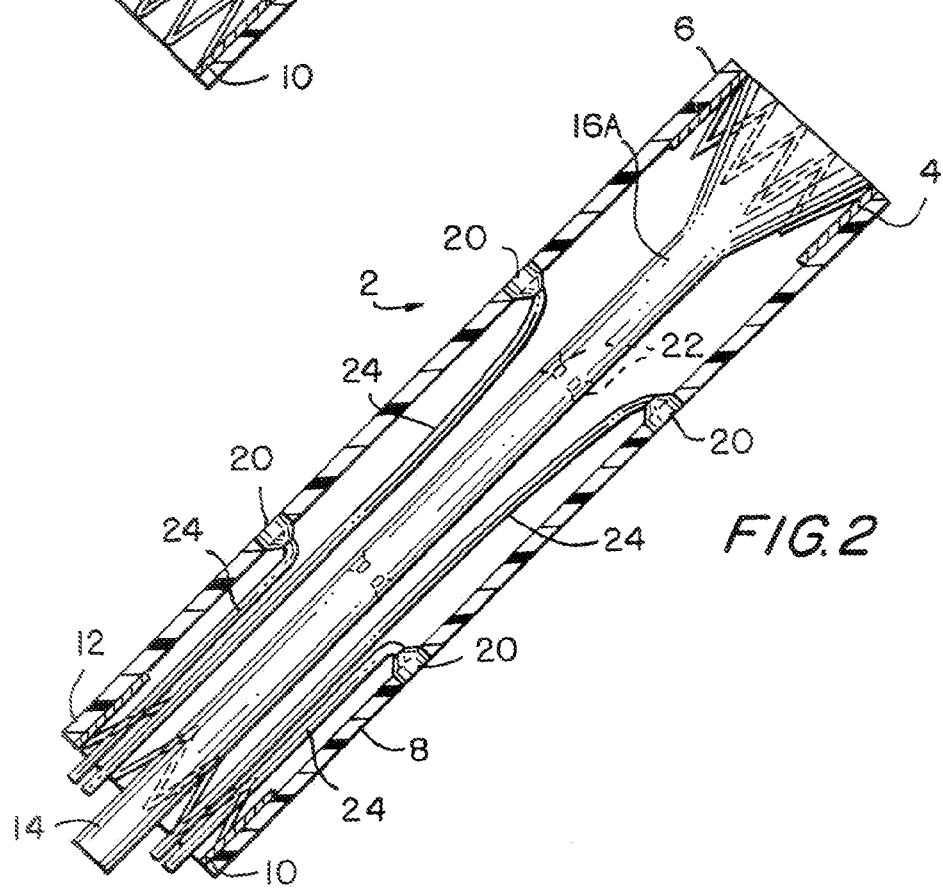
FIG. 2 is a partly cross-sectional view of another embodiment of the invention.

Also, as shown in FIG. 2, the distal portion 14 of valve member 16A may optionally extend to or through tubular member distal end 12, whereby food from a patient's esophagus (not shown), i.e., ingested food, would not be contacted by gastric acid or fluid within stent 2 or by digestive enzymes within the duodenum (not shown). If it were desired to have some food contact some gastric acid or fluid or digestive enzymes within a distally extending valve member distal portion 14, valve member distal portion 14 could have some one-way valves 22, dependent upon the amount of contact desired. It is within the scope of the invention that valve member distal portion 14 could extend as far as up to about 75% of the small bowel, preferably from about 25 to about 250 cm into the duodenum or beyond.

It is within the scope of the invention that one-way valves 20 could be in fluid connection with tubes 24 that would extend distally to a point substantially near or distal to distal end 12.

One skilled in the art would appreciate the various aspects of the stent of the invention, e.g., the length of valve member 16, the number and position of one-way valves 20 and 22, and the use of tubing 24 connected to valves 20, can be varied to achieve a desired result in terms of when ingested food is contacted by gastric fluid and to what extent.

Figure 3:
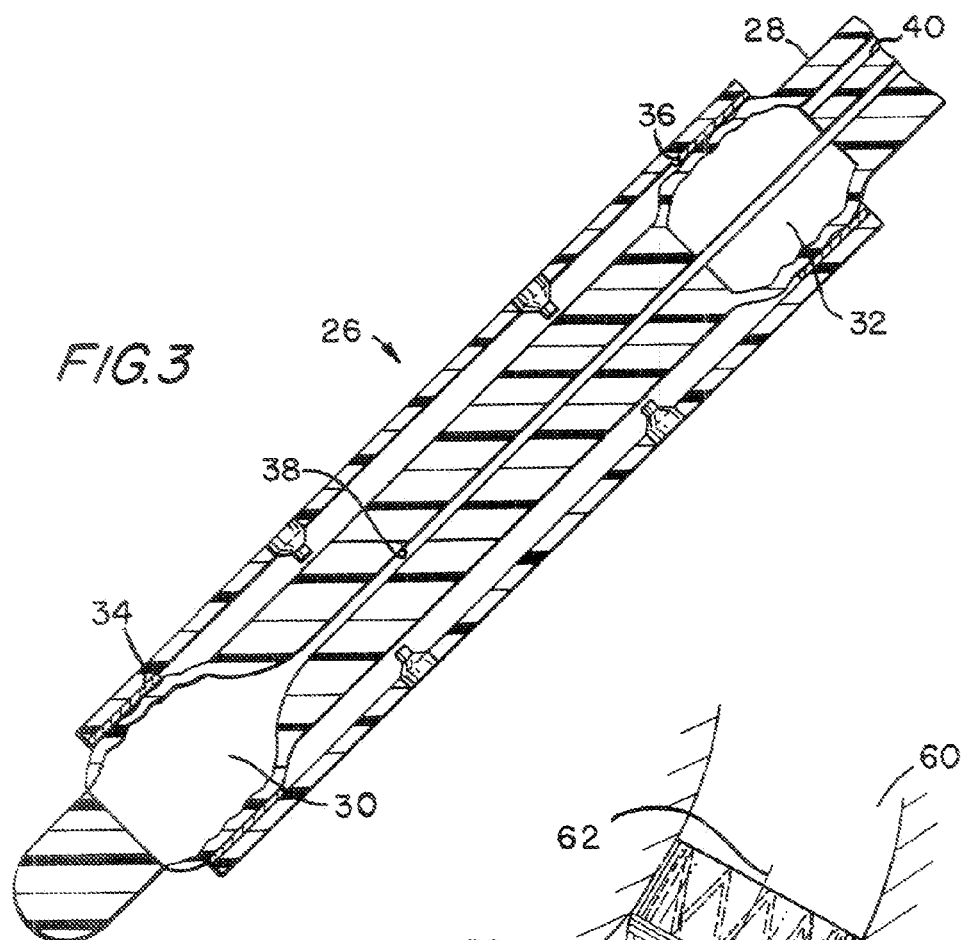
FIG. 3 is a cross-sectional view of an embodiment of the invention on a delivery catheter.

FIG. 3 is a cross-sectional view of a stent 26 on a delivery catheter 28. Catheter 28 comprises annular dilatation balloons 30 and 32 to expand stent members 34 and 36 once stent 26 is in position within a patient. Balloons 30 and 32 are inflated either sequentially or simultaneously through inflation lumens 38 and 40 to cause stent members 34 and 36 to expand to hold stent 26 in the desired position. Then, balloons 30 and 32 are deflated and catheter 28 is withdrawn.

Figure 4:
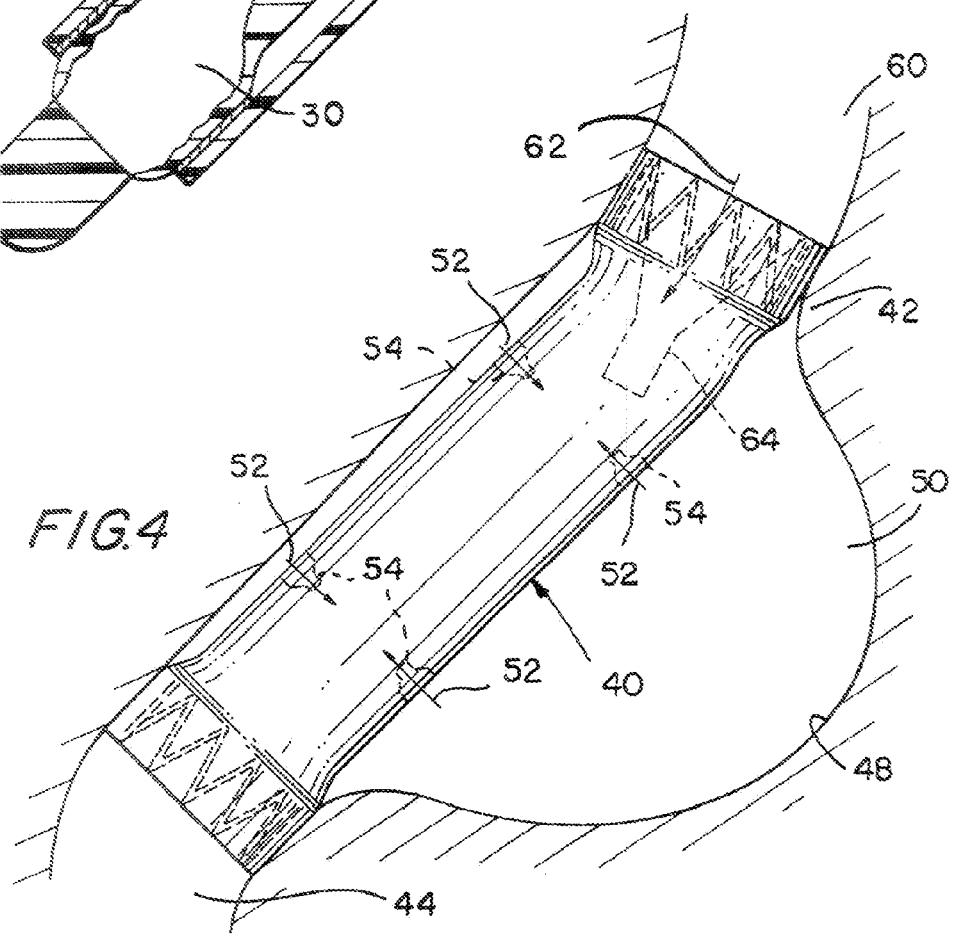
FIG. 4 is a partly cross-sectional view of an embodiment of the invention in position in a patient.

In FIG. 4 a stent 40 is shown in position, extending from a patient's gastro-esophageal junction 42 to the patient's duodenum 44. Gastric juices generated in the lining 48 of the stomach 50 flow in the direction of arrows 52 through one-way valves 54 into stent 40 and then into duodenum 44. Food or liquids from the esophagus 60 move in direction of arrow 62 through one-way valve 64 into stent 40 and then into duodenum 44, without direct contact with stomach 46.

The width, length, and other parameters of the stent of the invention will vary, especially according to the patient, as one skilled in the art would appreciate. The overall length of the stent will be from about 10 to about 40 cm, preferably from about 12 to about 30 cm, and the expanded diameter will be from about 1.5 to about 4 cm, preferably from about 2 to about 3 cm. The number and placement of one-way valves in each of the stent tubular member 8 or distally extending valve member 16 will vary from 1 to about 50, preferably from about 4 to about 40. The actual number will depend upon factors such as the size of each valve, the overall length of the stent member or valve member, the volume of fluid expected, etc.

Materials useful according to the inventor include biocompatible material such as stainless steel or nitinol and acid resistant polymers.

It will be further apparent to one skilled in this art that the improvements provided for in the present invention, while described with relation to certain specific physical embodiments also lend themselves to being applied in other physical arrangements not specifically provided for herein, which are nonetheless with the spirit and scope of the invention taught here.

We claim:

1. A device for insertion into a patient for bypassing a stomach of the patient, the device comprising:
    a tubular member having a proximal end, a distal end, and an outer wall, the tubular member defining a lumen extending therethrough;
    a first stent member positioned at the tubular member proximal end; and
    a second stent member positioned at the tubular member distal end,
    wherein the first stent member and the second stent member are configured such that, upon insertion of the device into patient, the first stent member can be disposed adjacent to and engage the gastro-esophageal junction of the patient and the second stent member can be disposed adjacent to and engage the duodenum of the patient; and
    further wherein the tubular member, the first stent member, and the second stent member are configured such that, after insertion and during operation of the device, liquids and solids entering the device via the first stent member can flow through the lumen and exit from the device via the second stent member without the outer wall of the tubular member contacting a wall of the patient's stomach, thereby bypassing the stomach.

2. The device of claim 1, wherein the first and second stent members comprise expandable structures.

3. The device of claim 2, wherein the first and second stent members are each self-expanding.

4. The device of claim 2, wherein the first and second stent members are each expandable or self-expanding.

5. The device of claim 1, wherein at least one of the first and second stent members comprises a one-way valve member with regard to liquid or solids entering the lumen of the tubular member.

6. The device of claim 5, wherein the valve member has a distal section that extends distally to or past the distal end of the tubular member.

7. The device of claim 6, wherein the distal section has one or more lateral openings to permit one-way liquid flow.

8. The device of claim 7, wherein the lateral openings comprise oneway valves to permit gastric fluid to enter the distal section.

9. The device of claim 1, wherein the outer wall of the tubular member defines one or more lateral openings therein to permit one-way liquid flow from outside of the outer wall of the tubular member into the lumen of the tubular member.

10. The device of claim 9, wherein the lateral openings comprise one-way valves to permit gastric fluid to enter the lumen of the tubular member.

11. The device of claim 10, wherein at least one of the one-way valves is in fluid communication with tubing that extends distally.

12. The device of claim 11, wherein the tubing extends to or past the distal end of the tubular member.

13. The device of claim 1, wherein the tubular member, the first stent, and the second stent are formed from biocompatible, acid-resistant materials.

14. The device of claim 1, wherein the tubular member includes a substantially liquid impervious coating or covering.

15. The device of claim 1, wherein the first stent member is capable of engaging the patient's gastro-esophageal junction and the second stent member is capable of engaging the patient's duodenum.

16. A device for insertion into a patient for bypassing the stomach of the patient, the device comprising:
    a tubular member having a proximal end, a distal end, and an outer wall and defining a lumen extending therethrough;
    a first stent member positioned at the tubular member proximal end; and
    a second stent member positioned at the tubular member distal end,
    wherein the tubular member, the first stent member, and the second stent member are configured such that, after insertion of the device into a patient and during operation of the device, the first stent member can engage the gastro-esophageal junction of the patent, the second stent member can engage the duodenum of the patient, and liquids and solids entering the device via the first stent member can flow through the lumen and exit from the device via the second stent member without the outer wall of the tubular member functionally engaging a wall of the patient's stomach, thereby bypassing the patient's stomach.

17. The device of claim 16, wherein the first and second stent members comprise expandable structures.

18. The device of claim 17, wherein the first and second stent are each self-expanding.

19. The device of claim 17, wherein the first and second stent members are each expandable or self-expanding.

20. The device of claim 16, wherein at least one of the first and second stent members comprises a one-way valve member with regard to liquid or solids entering the lumen of the tubular member.

21. The device of claim 20, wherein the valve member has a distal section that extends distally to or past the distal end of the tubular member.

22. The device of claim 21, wherein the distal section has one or more lateral openings to permit one-way liquid flow.

23. The device of claim 22, wherein the lateral openings comprise one-way valves to permit gastric fluid to enter the distal section.

24. The device of claim 16, wherein the outer wall of the tubular member defines one or more lateral openings therein to permit one-way liquid flow from outside of the outer wall of the tubular member into the lumen of the tubular member.

25. The device of claim 24, wherein the lateral openings comprise one-way valves to permit gastric fluid to enter the lumen of the tubular member.

26. The device of claim 25, wherein at least one of the one-way valves is in fluid communication with tubing that extends distally.

27. The device of claim 26, wherein the tubing extends to or past the distal end of the tubular member.

28. The device of claim 16, wherein the tubular member, the first stent, and the second stent are formed from biocompatible, acid-resistant materials.

29. The device of claim 16, wherein the tubular member includes a substantially liquid impervious coating or covering.

30. A device for insertion into a patient for bypassing the stomach of the patient, the device comprising:

a tubular member having a proximal end, a distal end, and an outer wall, the tubular member defining a lumen extending therethrough;

a first stent member positioned at the tubular member proximal end; and a second stent member positioned at the tubular member distal end, wherein the tubular member, the first stent member, and the second stent member are configured such that, after insertion of the device into a stomach of a patient and during operation of the device, the tubular member can extend from adjacent the gastro-esophageal junction of the patient to at least adjacent the duodenum of the patient without the outer wall of the tubular member contacting a wall of the patient's stomach, and such that liquids and solids entering the device via the first stent member can flow through the lumen and exit from the device via the second stent member, thereby bypassing the patient's stomach.

31. A device for insertion into a patient for bypassing the stomach of the patient, the device comprising:

a tubular member having a proximal end, and an outer wall and defining a lumen extending therethrough, the tubular member comprising a substantially liquid impervious coating or covering;

a first stent member positioned at the tubular member proximal end; and a second stem member positioned at the tubular member distal end, wherein me tubular member, the first stent member, and the second stent member are configured such that, after insertion of the device into a patient, the first stent member can engage the gastro-esophageal junction of the patient, the second stent member can engage the duodenum of the patient, and wherein liquids and solids entering the device via the first stem member can flow through the lumen and exit from the device via the second stent member without the outer wall of the tubular member functionally engaging a wall of the patient's stomach, thereby bypassing Patient's the stomach.

* * * * *

UNITED STATES PATENT AND TRADEMARK OFFICE
CERTIFICATE OF CORRECTION

PATENT NO. : 7,211,114 B2 Page 1 of 1
APPLICATION NO. : 10/229400
DATED : May 1, 2007
INVENTOR(S) : William H. Dippert It is certified that error appears in the above-identified patent and that said Letters Patent is hereby corrected as shown below:

In Claim 16, column 4, line 65, "patent" should be -- patient --;

In Claim 31, column 6, line 22, -- a distal end -- should be inserted between "end," and "and";

In Claim 31, column 6, line 28, "stem" should be -- stent --;

In Claim 31, column 6, line 30, "me" should be -- the --; and

In Claim 31, column 6, line 40, "Patient's the" should be -- the patient's --.

Signed and Sealed this

Eleventh Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,211,114 B2  Page 1 of 1
APPLICATION NO. : 10/229400
DATED : May 1, 2007
INVENTOR(S) : Marc Bessler et al.

It is certified that error appears in the above-identified patent and that said Letters Patent is hereby corrected as shown below:

In Claim 16, column 4, line 65, "patent" should be -- patient --;

In Claim 31, column 6, line 22, -- a distal end -- should be inserted between "end," and "and";

In Claim 31, column 6, line 28, "stem" should be -- stent --;

In Claim 31, column 6, line 30, "me" should be -- the --; and

In Claim 31, column 6, line 40, "Patient's the" should be -- the patient's --.

This certificate supersedes the Certificate of Correction issued December 11, 2007.

Signed and Sealed this

Twenty-third Day of September, 2008

JON W. DUDAS
*Director of the United States Patent and Trademark Office*